US012622996B2

(12) United States Patent
Waite et al.

(10) Patent No.: US 12,622,996 B2
(45) Date of Patent: May 12, 2026

(54) WOUND DRESSING COMPOSITIONS AND USES THEREOF

(71) Applicant: SYSTAGENIX WOUND MANAGEMENT, LIMITED, West Sussex (GB)

(72) Inventors: Alexander Waite, Cowling (GB); Carrina Ward, Gargrave (GB)

(73) Assignee: Systagenix Wound Management, Limited, West Sussex (GB)

( * ) Notice: Subject to any disclaimer, the term of this patent is extended or adjusted under 35 U.S.C. 154(b) by 776 days.

(21) Appl. No.: 17/278,875

(22) PCT Filed: Sep. 24, 2019

(86) PCT No.: PCT/IB2019/058096

§ 371 (c)(1),
(2) Date: Mar. 23, 2021

(87) PCT Pub. No.: WO2020/065531

PCT Pub. Date: Apr. 2, 2020

(65) Prior Publication Data

US 2022/0047771 A1 Feb. 17, 2022

Related U.S. Application Data

(60) Provisional application No. 62/736,116, filed on Sep. 25, 2018.

(51) Int. Cl.

| | |
|---|---|
| ***A61L 15/56*** | (2006.01) |
| ***A61F 13/00*** | (2024.01) |
| ***A61F 13/01*** | (2024.01) |
| ***A61L 15/26*** | (2006.01) |
| ***A61L 15/42*** | (2006.01) |
| ***A61L 15/60*** | (2006.01) |

(52) U.S. Cl.

CPC ........ *A61L 15/56* (2013.01); *A61F 13/00059* (2013.01); *A61F 13/00072* (2013.01); *A61F 13/01029* (2024.01); *A61F 13/01042* (2024.01); *A61L 15/26* (2013.01); *A61L 15/425* (2013.01); *A61L 15/60* (2013.01); *A61F 2013/00238* (2013.01); *A61F 2013/00255* (2013.01)

(58) Field of Classification Search

None

See application file for complete search history.

(56) References Cited

U.S. PATENT DOCUMENTS

| | | | | |
|---|---|---|---|---|
| 1,355,846 | A | 10/1920 | Rannells | |
| 2,547,758 | A | 4/1951 | Keeling | |
| 2,632,443 | A | 3/1953 | Lesher | |
| 2,682,873 | A | 7/1954 | Evans et al. | |
| 2,764,976 | A * | 10/1956 | Skiles, Jr. | A61L 15/48 422/1 |
| 2,910,763 | A | 11/1959 | Lauterbach | |
| 2,969,057 | A | 1/1961 | Simmons | |
| 3,066,672 | A | 12/1962 | Crosby, Jr. et al. | |
| 3,367,332 | A | 2/1968 | Groves | |
| 3,520,300 | A | 7/1970 | Flower, Jr. | |
| 3,568,675 | A | 3/1971 | Harvey | |
| 3,648,692 | A | 3/1972 | Wheeler | |
| 3,682,180 | A | 8/1972 | McFarlane | |
| 3,826,254 | A | 7/1974 | Mellor | |
| 4,080,970 | A | 3/1978 | Miller | |
| 4,096,853 | A | 6/1978 | Weigand | |
| 4,139,004 | A | 2/1979 | Gonzalez, Jr. | |
| 4,165,748 | A | 8/1979 | Johnson | |
| 4,184,510 | A | 1/1980 | Murry et al. | |
| 4,233,969 | A | 11/1980 | Lock et al. | |
| 4,245,630 | A | 1/1981 | Lloyd et al. | |
| 4,256,109 | A | 3/1981 | Nichols | |
| 4,261,363 | A | 4/1981 | Russo | |
| 4,275,721 | A | 6/1981 | Olson | |
| 4,284,079 | A | 8/1981 | Adair | |
| 4,297,995 | A | 11/1981 | Golub | |
| 4,333,468 | A | 6/1982 | Geist | |
| 4,341,207 | A * | 7/1982 | Steer | A61F 13/0213 602/56 |
| 4,373,519 | A | 2/1983 | Errede et al. | |

(Continued)

FOREIGN PATENT DOCUMENTS

| | | | |
|---|---|---|---|
| AU | 550575 | B2 | 3/1986 |
| AU | 745271 | B2 | 3/2002 |

(Continued)

OTHER PUBLICATIONS

Griess Reagent Kit for nitrite determination (Available Jul. 9, 2003) (Year: 2023).*

Frank et al. (Nitric oxide drives skin repair: novel functions of an established mediator, Kidney Int Mar. 2002; 61(3):882-8) (Year: 2002).*

Griess Reagent Kit for nitrite determination (Available Jul. 9, 2003) (Year: 2003).*

International Search Report and Written Opinion on International Patent Application No. PCT/IB2019/058096 dated Dec. 9, 2019 (13 pages).

(Continued)

*Primary Examiner* — Melissa S Mercier

(57) ABSTRACT

The present disclosure relates generally to wound dressing compositions that detect nitric oxide production in a wound upon application. The wound dressing composition comprises a first layer comprising an absorbent layer, a second layer comprising a reaction pad, a third layer comprising a transparent backing film, and optionally a fourth layer comprising a wicking layer. In the wound dressing composition, the second layer comprises a reaction pad of a dried reaction mixture to detect the presence of nitric oxide in a wound. The wound dressing composition can be a visual indicator of the presence of nitric oxide in a wound; a visual indicator of the wounds healing status.

20 Claims, 1 Drawing Sheet

(56) References Cited

U.S. PATENT DOCUMENTS 4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2006/0120976 A1* 6/2006 Brown .................. A61K 31/44 424/59
2010/0178203 A1 7/2010 Kane et al.
2014/0058309 A1 2/2014 Addison et al.
2014/0065606 A1* 3/2014 Green .................... G01N 33/84 436/116
2014/0163491 A1 6/2014 Schuessler et al.
2015/0080788 A1 3/2015 Blott et al.
2016/0106348 A1 4/2016 Yang et al.
2018/0021459 A1* 1/2018 Hunt .................... G01N 33/543 424/9.1
2018/0100807 A1* 4/2018 Abdo ..................... C09D 11/50

FOREIGN PATENT DOCUMENTS

AU 755496 B2 12/2002
CA 2005436 A1 6/1990
DE 2640413 A1 3/1978
DE 4306478 A1 9/1994
DE 29504378 U1 9/1995
EP 0100148 A1 2/1984
EP 117632 A2 9/1984
EP 161865 A2 11/1985
EP 358302 A2 3/1990
EP 1018967 A1 7/2000
GB 692578 A 6/1953
GB 2195255 A 4/1988
GB 2197789 A 6/1988
GB 2220357 A 1/1990
GB 2235877 A 3/1991
GB 2329127 A 3/1999
GB 2333965 A 8/1999
JP 4129536 B2 8/2008
SG 71559 4/2002
WO 80/02182 A1 10/1980
WO 8704626 A1 8/1987
WO 90010424 A1 9/1990
WO 93009727 A1 5/1993
WO 94020041 A1 9/1994
WO 9605873 A1 2/1996
WO 9718007 A1 5/1997
WO 9913793 A1 3/1999
WO WO-2017173069 A1 * 10/2017 ............. A61L 15/38

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; “When wounds Won’t Heal” RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

(56) References Cited

OTHER PUBLICATIONS

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

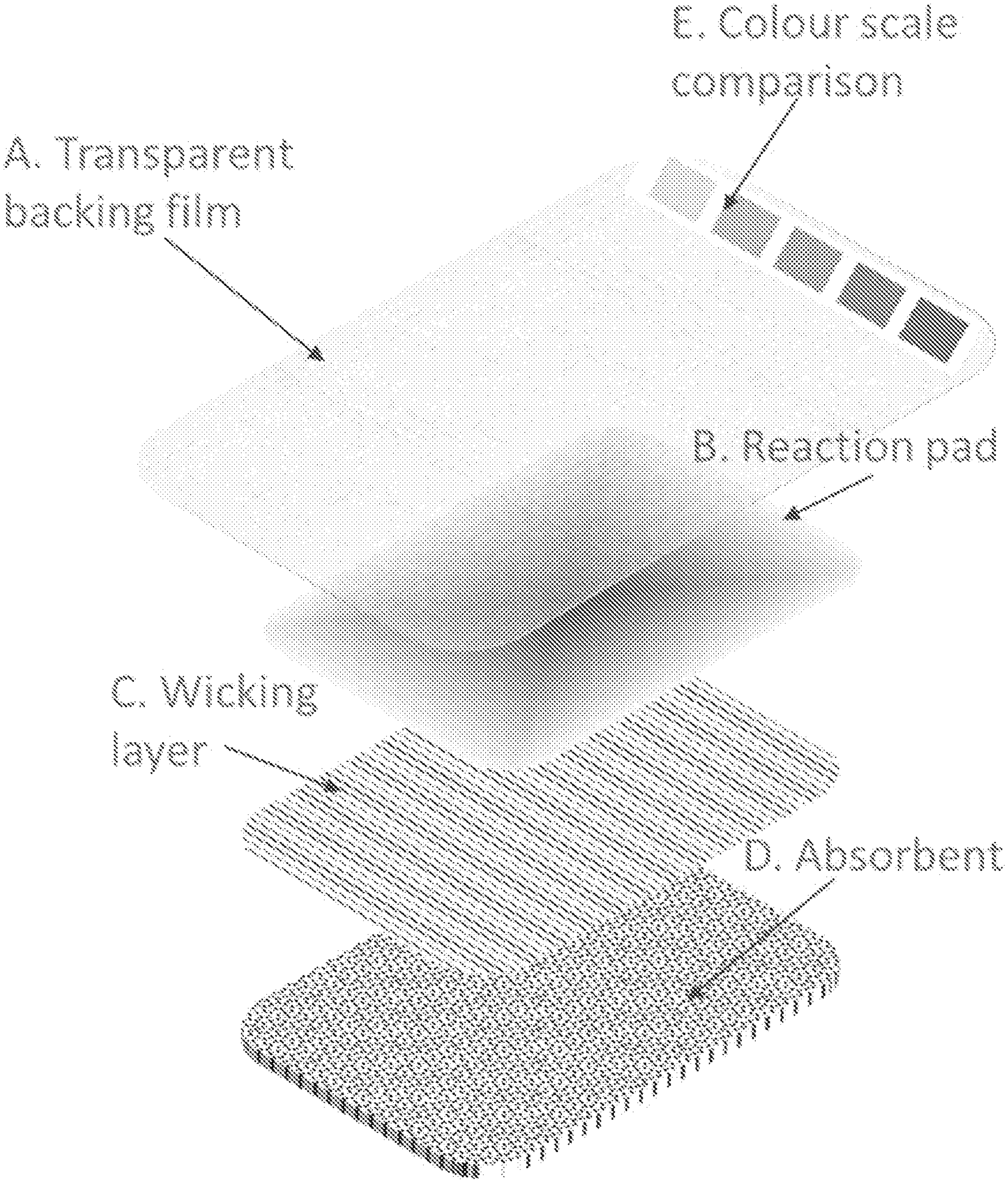
E. Colour scale comparison
A. Transparent backing film
B. Reaction pad
C. Wicking layer
D. Absorbent

WOUND DRESSING COMPOSITIONS AND USES THEREOF

CROSS-REFERENCE TO RELATED PATENT APPLICATIONS

This application is a U.S. National Phase Application under 35 U.S.C. § 371 of International Patent Application No. PCT/IB2019/058096, filed on Sep. 24, 2019, which claims the benefit of and priority to U.S. Provisional Appl. No. 62/736,116, filed Sep. 25, 2018, the entire contents of each of which is incorporated by reference herein in its entirety.

TECHNICAL FIELD

The present technology relates generally to wound dressing compositions that detect nitric oxide production in a wound upon application, and over time and methods of using the same. Kits for use in practicing the methods are also provided.

BACKGROUND

Nitric oxide is a signaling molecule vital to key processes in wound healing such as angiogenesis, vasodilation, and immune response. The nitric oxide levels in a wound and the wound fluid is useful for determining the state of a wound. Specifically, nitric oxide levels at the wound site can indicate whether the conditions within the wound are conducive to healing. Nitric oxide levels can be factored together with clinician judgement to make therapeutic decisions about wound care. Currently, there is an unmet need for wound dressing products that detect nitric oxide production in a wound upon application, and over time.

SUMMARY

In one aspect, the present disclosure provides a wound dressing composition comprising a first layer, a second layer, and a third layer, wherein the first layer comprises an absorbent layer, the second layer comprises a reaction pad, and the third layer comprises a transparent backing film. In some embodiments of the wound dressing composition of the present technology, the wound-facing side of the third layer is coupled with the environmental-facing side of the second layer, and wherein the wound-facing side of the second layer is coupled with the environmental-facing side of the first layer.

In another aspect, the present disclosure provides a wound dressing composition comprising a first layer, a second layer, a third layer, and a fourth layer, wherein the first layer comprises an absorbent layer, the second layer comprises a reaction pad, the third layer comprises a transparent backing film, and the fourth layer comprises a wicking layer. In some embodiments of the wound dressing composition of the present technology, the wound-facing side of the third layer is coupled with the environmental-facing side of the second layer, wherein the wound-facing side of the second layer is coupled with the environmental-facing side of the fourth layer, and wherein the wound-facing side of the fourth layer is coupled with the environmental-facing side of the first layer.

Additionally or alternatively, in some embodiments, the first layer is selected from the group consisting of a foam pad, a gauze, a nonwoven fabric, a superabsorbent, a hydrogel, and any combination thereof. Additionally or alternatively, in some embodiments, the foam pad is a polyurethane foam pad.

Additionally or alternatively, in some embodiments, the second layer is selected from the group consisting of a gauze, a non-woven fabric, a filter paper, and any combination thereof.

Additionally or alternatively, in some embodiments, the third layer is selected from the group consisting of polyurethane, polyalkoxy alkyl acrylate, polyalkoxy alkyl methacrylate, or any combination thereof.

Additionally or alternatively, in some embodiments, the fourth layer is selected from the group consisting of a superabsorbent polymer, a non-woven carboxymethyl cellulose (CMC) pad, polyester, rayon, nylon, or any combination thereof.

Additionally or alternatively, in some embodiments, a colorimetric indicator strip is included on the environmental-facing side of the third layer.

Additionally or alternatively, in some embodiments, the second layer comprises a dried reaction mixture of a first reagent and a second reagent, wherein the first reagent has the formula:

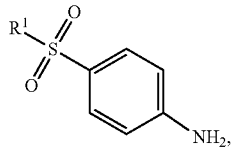

and $R^1$ is $NH_2$ or OH,
and the second reagent has the formula:

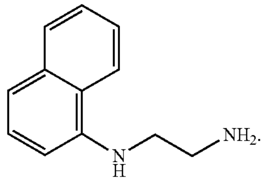 [SMILES: NCCNc1cccc2ccccc12]

Additionally or alternatively, in some embodiments, the thickness of each of the first layer, the second layer, and optionally the fourth layer is independently about 15 μm to about 500 μm. Additionally or alternatively, in some embodiments, the thickness of the third layer is about 10 μm to about 1000 μm, about 15 μm to about 500 μm. or about 100 μm to about 500 μm.

Additionally or alternatively, in some embodiments, the third layer extends beyond each of the first layer, the second layer, and optionally the fourth layer, such that a marginal region of width extends around the wound dressing composition from about 1 mm to about 50 mm, or about 5 mm to about 20 mm. Additionally or alternatively, in some embodiments, the wound-facing side of the extended region of the third layer is coated with a pressure sensitive medical grade adhesive.

Additionally or alternatively, in some embodiments, the wound dressing composition is sterile and packaged in a microorganism-impermeable container.

In another aspect, the present disclosure provides a method for detecting nitric oxide levels in a wound in a subject in need thereof, comprising administering to the wound any and all embodiments of a wound dressing composition disclosed herein that comprises a first layer, a second layer, and a third layer, wherein the first layer comprises an absorbent layer, the second layer comprises a reaction pad, and the third layer comprises a transparent backing film; and detecting a colorimetric change in the second layer, wherein the colorimetric change indicates the presence of nitric oxide in the wound.

In another aspect, the present disclosure provides a method for detecting nitric oxide levels in a wound in a subject in need thereof, comprising administering to the wound any and all embodiments of a wound dressing composition disclosed herein that comprises a first layer, a second layer, a third layer, and a fourth layer, wherein the first layer comprises an absorbent layer, the second layer comprises a reaction pad, the third layer comprises a transparent backing film, and the fourth layer comprises a wicking layer; and detecting a colorimetric change in the second layer, wherein the colorimetric change indicates the presence of nitric oxide in the wound.

Additionally or alternatively, in some embodiments, the method further comprises determining nitric oxide levels by comparing the color of the second layer to an indicator strip located on the third layer. The indicator strip is located on the environmental-facing side of the third layer. Additionally or alternatively, in some embodiments, the method further comprises determining nitric oxide levels by comparing the color of the second layer to an indicator strip present on a microorganism-impermeable container for the wound dressing composition.

In any embodiment disclosed herein, the wound may be acute or chronic.

Additionally or alternatively, in some embodiments, the method further comprises determining nitric oxide levels by receiving an image from an image capture device, comparing a value of at least one feature of the image to a threshold value, and providing an output responsive to comparing the value of the at least one feature to the threshold value, wherein the output is indicative of wound healing status.

Additionally or alternatively, in some embodiments, the method further comprises determining a first nitric oxide level when the wound dressing composition is administered to the subject in need thereof, and determining a second nitric oxide level about 1 minute to about 24 hours after the wound dressing composition is administered to the subject in need thereof.

In another aspect, the present disclosure provides a method for monitoring the efficacy of a therapeutic intervention for a subject in need thereof, where the method includes administering to the wound a wound dressing composition of any embodiment disclosed herein, detecting a colorimetric change in the second layer, wherein the colorimetric change indicates the presence of nitric oxide in the wound, determining a first nitric oxide level when the wound dressing composition is administered to the subject in need thereof, and determining a second nitric oxide level about 1 minute to about 24 hours after the wound dressing composition is administered to the subject; wherein the therapeutic intervention is effective when the second nitric oxide level is greater compared to the first nitric oxide level.

In another aspect, the present disclosure provides a method for monitoring the efficacy of a therapeutic intervention for a subject in need thereof, where the method includes administering to the wound a wound dressing composition of any embodiment disclosed herein, detecting a colorimetric change in the second layer, wherein the colorimetric change indicates the presence of nitric oxide in the wound, and determining a nitric oxide level when the wound dressing composition is administered to the subject in need thereof; wherein the therapeutic intervention is effective when the nitric oxide level is increased compared to a pre-determined reference level.

In another aspect, the present disclosure provides a method for making a wound dressing composition comprising, providing a first layer comprising an absorbent pad, providing a second layer comprising a reaction pad, providing a third layer comprising a transparent backing film, and combining the first layer, the second layer, and the third layer to form the wound dressing composition, wherein each of the first layer, the second layer, and the third layer comprises a wound-facing side and an environmental-facing side.

In another aspect, the present disclosure provides a method for making a wound dressing composition comprising, providing a first layer comprising an absorbent pad, providing a second layer comprising a reaction pad, providing a third layer comprising a transparent backing film, providing a fourth layer comprising a wicking layer, and combining the first layer, the second layer, the third layer, and the fourth layer to make the wound dressing composition, wherein each of the first layer, the second layer, the third layer, and the fourth layer comprises a wound-facing side and an environmental-facing side.

Also provided herein are kits comprising the wound dressing compositions of any embodiment described herein and instructions for use.

BRIEF DESCRIPTION OF THE DRAWINGS

FIG. 1 shows a diagrammatic representation of the components of the wound dressing composition of the present technology.

DETAILED DESCRIPTION

It is to be appreciated that certain aspects, modes, embodiments, variations and features of the present methods are described below in various levels of detail in order to provide a substantial understanding of the present technology.

A wound can become infected by microbes. An infected wound is a wound in which bacteria or other microorganisms have colonized, causing a deterioration and delay in the healing of the wound.

The present disclosure provides wound dressing compositions that detect nitric oxide production in a wound upon application, and over time. Nitric oxide is a signaling molecule vital to key processes in wound healing such as angiogenesis, vasodilation, and immune response. Without early detection of nitric oxide in a wound, there is a risk of late therapeutic intervention for chronic wounds.

Definitions

The definitions of certain terms as used in this specification are provided below. Unless defined otherwise, all technical and scientific terms used herein generally have the same meaning as commonly understood by one of ordinary skill in the art to which this present technology belongs.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the terms "moisture vapor transmission rate" and "MVTR" will be understood by persons of ordinary skill in the art as a measure of the passage of water vapor through a substance of a given unit area and unit time. The most common international unit for the MVTR is $g/m^2$/day, wherein 1 day=24 hr.

As used herein, the term "basis weight" will be understood by persons of ordinary skill in the art as a measure of the weight of a layer expressed in terms of the weight of the wound dressing compositions of the present technology.

As used herein, the term "pharmaceutically acceptable salts" of reagents disclosed herein are within the scope of the present technology include acid or base addition salts which retain the desired pharmacological activity and is not biologically undesirable (e.g., the salt is not unduly toxic, allergenic, or irritating, and is bioavailable). When the reagent of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the reagent of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the reagents or by separately reacting the purified reagent in its free base or free acid form with a suitable acid or base, respectively, and isolating the salt thus formed.

As used herein, the term "substantial" and "substantially" includes total but also less than total. In the context of the wound dressing of the present technology, the third layer which comprises a transparent backing film is substantially liquid and microorganism impermeable.

As used herein, the "administration" of a wound dressing composition to a subject includes any route of introducing or delivering to a subject a wound dressing composition to perform its intended function. Administration can be carried out by any suitable route, including but not limited to, topical administration. Administration includes self-administration and the administration by another.

As used herein, the terms "individual", "patient", or "subject" can be an individual organism, a vertebrate, a mammal, or a human. In some embodiments, the individual, patient or subject is a human.

"Treating" or "treatment" as used herein covers the treatment of a wound described herein, in a subject, such as a human, and includes: (i) inhibiting a wound, i.e., arresting its development; (ii) relieving a wound, i.e., causing regression of the wound; (iii) slowing progression of the wound; and/or (iv) inhibiting, relieving, or slowing progression of one or more symptoms of the wound. In some embodiments, treatment means that the symptoms associated with the wound are, e.g., alleviated, reduced, cured, or placed in a state of remission.

It is also to be appreciated that the various modes of treatment of wounds as described herein are intended to mean "substantial," which includes total but also less than total treatment, and wherein some biologically or medically relevant result is achieved. The treatment may be a continuous prolonged treatment for a chronic wound or a single, or few time administrations for the treatment of an acute wound.

The Wound Dressing Composition of the Present Technology

The First Layer

The present disclosure provides a wound dressing composition comprising a first layer wherein the first layer comprises an absorbent layer for absorbing wound fluids, serum or blood in the wound interface.

In any embodiment disclosed herein, the first layer comprises a wound-facing side and an environmental-facing side.

In any embodiment disclosed herein, the first layer is selected from the group consisting of a foam pad, a gauze, a nonwoven fabric, a superabsorbent, a hydrogel, and any combination thereof. Additionally or alternatively, the first layer comprises a foam pad, such as an open celled hydrophilic polyurethane foam prepared in accordance with EP-A-0541391. Additionally or alternatively, in some embodiments, the thickness of the first layer may be in the range of about 15 μm to about 500 μm, with a basis weight of about 50 $g/m^2$ to about 500 $g/m^2$. Additionally or alternatively, in some embodiments, the thickness of the first layer may be in the range of about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 52 μm, about 54 μm, about 56 μm, about 58 μm, about 60 μm, about 62 μm, about 64 μm, about 66 μm, about 68 μm, about 70 μm, about 72 μm, about 74 μm, about 76 μm, about 78 μm, about 80 μm, about 82 μm, about 84 μm, about 86 μm, about 88 μm, about 90 μm, about 92 μm, about 94 μm, about 96 μm, about 98 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 210 μm, about 220 μm, about 230 μm, about 240 μm, about 250

μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, or any range including and/or in between any two of the preceding values. Additionally or alternatively, in some embodiments, the first layer may be in the range of about 50 $g/m^2$, about 60 $g/m^2$, about 70 $g/m^2$, about 80 $g/m^2$, about 90 $g/m^2$, about 100 $g/m^2$, about 110 $g/m^2$, about 120 $g/m^2$, about 130 $g/m^2$, about 140 $g/m^2$, about 150 $g/m^2$, about 160 $g/m^2$, about 170 $g/m^2$, about 180 $g/m^2$, about 190 $g/m^2$, about 200 $g/m^2$, about 220 $g/m^2$, about 240 $g/m^2$, about 260 $g/m^2$, about 280 $g/m^2$, about 300 $g/m^2$, about 320 $g/m^2$, about 340 $g/m^2$, about 360 $g/m^2$, about 380 $g/m^2$, about 400 $g/m^2$, about 420 $g/m^2$, about 440 $g/m^2$, about 460 $g/m^2$, about 480 $g/m^2$, about 500 $g/m^2$, or any range including and/or in between any two of the preceding values.

In any embodiment disclosed herein, the first layer may comprise about 0.001 wt. % to about 5 wt. % of an at least one antimicrobial agent. Additionally or alternatively, in some embodiments the at least one antimicrobial agent may comprise about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 2 wt. %, about 3 wt. %, about 4 wt. %, about 5 wt. %, or any range including and/or in between any two of the preceding values. Additionally or alternatively, in some embodiments the at least one antimicrobial agent is selected from the group consisting of tetracycline, penicillins, terramycins, erythromycin, bacitracin, neomycin, polymycin B, mupirocin, clindamycin, colloidal silver, silver salts, silver sulfadiazine, chlorhexidine, povidone iodine, triclosan, sucralfate, quaternary ammonium salts, and any combination thereof.

The Second Layer

The present disclosure provides a wound dressing composition comprising a second layer wherein the second layer comprises a reaction pad, which comprises a first reagent and a second reagent, wherein a colorimetric chemical reaction occurs between the first reagent and the second reagent, thereby indicating the presence of nitric oxide in a wound.

In any embodiment disclosed herein, the second layer comprises a wound-facing side and an environmental-facing side.

In any embodiment disclosed herein, the reaction pad of the second layer may selected from the group consisting of a gauze, a nonwoven fabric, a filter paper, and any combination thereof. Additionally or alternatively, in some embodiments, the thickness of the second layer may be in the range of about 15 μm to about 500 μm. Additionally or alternatively, in some embodiments, the thickness of the second layer may be in the range of about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 52 μm, about 54 μm, about 56 μm, about 58 μm, about 60 μm, about 62 μm, about 64 μm, about 66 μm, about 68 μm, about 70 μm, about 72 μm, about 74 μm, about 76 μm, about 78 μm, about 80 μm, about 82 μm, about 84 μm, about 86 μm, about 88 μm, about 90 μm, about 92 μm, about 94 μm, about 96 μm, about 98 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, or any range including and/or in between any two of the preceding values.

In any embodiment disclosed herein, the second layer comprises a dried colorimetric reaction mixture of a first reagent represented by Formula I, and a second reagent represented by Formula II. Additionally or alternatively, the first reagent is represented by Formula I (I)

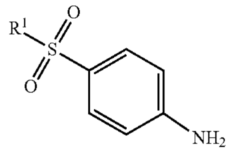

or a pharmaceutically acceptable salt thereof, where $R^1$ is $NH_2$ or OH. Additionally or alternatively, the first reagent is represented by Formula II (II)

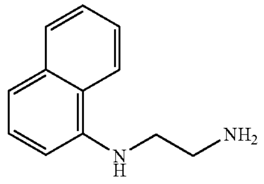

or a pharmaceutically acceptable salt thereof.

In any embodiment disclosed herein, the second layer may comprise about 0.1 wt. % to about 50 wt. % of the first reagent. Additionally or alternatively, in some embodiments the first reagent may comprise about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.2 wt. %, about 2.4 wt. %, about 2.6 wt. %, about 2.8 wt. %, about 3 wt. %, about 3.2 wt. %, about 3.4 wt. %, about 3.6 wt. %, about 3.8 wt. %, about 4 wt. %, about 4.2 wt. %, about 4.4 wt. %, about 4.6 wt. %, about 4.8 wt. %, about 5 wt. %, about 5.2 wt. %, about 5.4 wt. %, about 5.6 wt. %, about 5.8 wt. %, about 6 wt. %, about 6.2 wt. %, about 6.4 wt. %, about 6.6 wt. %, about 6.8 wt. %, about 7 wt. %, about 7.2 wt. %, about 7.4 wt. %, about 7.6 wt. %, about 7.8 wt. %, about 8 wt. %, about 8.2 wt. %, about 8.4 wt. %, about 8.6 wt. %, about 8.8 wt. %, about 9 wt. %, about 9.2 wt. %, about 9.4 wt. %, about 9.6 wt. %, about 9.8 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, or any range including and/or in between any two of the preceding values.

In any embodiment disclosed herein, the second layer may comprise about 0.01 wt. % to about 5 wt. % of the second reagent. Additionally or alternatively, in some embodiments the second reagent may comprise about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, or any range including and/or in between any two of the preceding values.

In any embodiment disclosed herein, the second layer may comprise a ratio of the first reagent to the second reagent of about 10:1.

The Third Layer

The present disclosure provides a wound dressing composition comprising a third layer wherein the third layer comprises a transparent backing film.

In any embodiment disclosed herein, the third layer comprises a wound-facing side and an environmental-facing side.

In any embodiment disclosed herein, the third layer may be composed of a material selected from the group consisting of polyurethanes, polyalkoxy alkyl acrylate, polyalkoxy alkyl methacrylates, and any combination thereof. Additionally or alternatively, in some embodiments, the thickness of the third layer may be in the range of about 10 μm to about 1000 μm, about 15 μm to about 500 μm, or about 100 μm to about 500 μm. Additionally or alternatively, in some embodiments, the thickness of the third layer may be in the range of about 10 μm, about 11 μm, about 12 μm, about 13 μm, about 14 μm, about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 52 μm, about 54 μm, about 56 μm, about 58 μm, about 60 μm, about 62 μm, about 64 μm, about 66 μm, about 68 μm, about 70 μm, about 72 μm, about 74 μm, about 76 μm, about 78 μm, about 80 μm, about 82 μm, about 84 μm, about 86 μm, about 88 μm, about 90 μm, about 92 μm, about 94 μm, about 96 μm, about 98 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, about 560 μm, about 570 μm, about 580 μm, about 590 μm, about 600 μm, about 610 μm, about 620 μm, about 630 μm, about 640 μm, about 650 μm, about 660 μm, about 670 μm, about 680 μm, about 690 μm, about 700 μm, about 710 μm, about 720 μm, about 730 μm, about 740 μm, about 750 μm, about 760 μm, about 770 μm, about 780 μm, about 790 μm, about 800 μm, about 810 μm, about 820 μm, about 830 μm, about 840 μm, about 850 μm, about 860 μm, about 870 μm, about 880 μm, about 890 μm, about 900 μm, about 910 μm, about 920 μm, about 930 μm, about 940 μm, about 950 μm, about 960 μm, about 970 μm, about 980 μm, about 990 μm, about 1000 μm, or any range including and/or in between any two of the preceding values.

In any embodiment disclosed herein, the third layer is substantially impermeable to liquid and wound exudate. Additionally or alternatively, the third layer is microorganism impermeable. Additionally or alternatively, the third layer is semi-permeable to water vapor. In any embodiment disclosed herein, the third layer may comprise a moisture vapor transmission rate (MVTR) of about 300 $g/m^2/24$ hrs to about 20,000 $g/m^2/24$ hrs, or about 500 $g/m^2/24$ hrs to about 2000 $g/m^2/24$ hrs at 37.5° C. at 100% to 10% relative humidity difference. Additionally or alternatively, the third layer may comprise a MVTR of about 300 $g/m^2/24$ hrs, about 350 $g/m^2/24$ hrs, about 400 $g/m^2/24$ hrs, about 450 $g/m^2/24$ hrs, about 500 $g/m^2/24$ hrs, about 550 $g/m^2/24$ hrs, about 600 $g/m^2/24$ hrs, about 650 $g/m^2/24$ hrs, about 700 $g/m^2/24$ hrs, about 750 $g/m^2/24$ hrs, about 800 $g/m^2/24$ hrs, about 850 $g/m^2/24$ hrs, about 900 $g/m^2/24$ hrs, about 950 $g/m^2/24$ hrs, about 1000 $g/m^2/24$ hrs, about 1100 $g/m^2/24$ hrs, about 1200 $g/m^2/24$ hrs, about 1300 $g/m^2/24$ hrs, about 1400 $g/m^2/24$ hrs, about 1500 $g/m^2/24$ hrs, about 1600 $g/m^2/24$ hrs, about 1700 $g/m^2/24$ hrs, about 1800 $g/m^2/24$ hrs, about 1900 $g/m^2/24$ hrs, about 2000 $g/m^2/24$ hrs, about 2200 $g/m^2/24$ hrs, about 2400 $g/m^2/24$ hrs, about 2600 $g/m^2/24$ hrs, about 2800 $g/m^2/24$ hrs, about 3000 $g/m^2/24$ hrs, about 3200 $g/m^2/24$ hrs, about 3400 $g/m^2/24$ hrs, about 3600 $g/m^2/24$ hrs, about 3800 $g/m^2/24$ hrs, about 4000 $g/m^2/24$ hrs, about 4200 $g/m^2/24$ hrs, about 4400 $g/m^2/24$ hrs, about 4600 $g/m^2/24$ hrs, about 4800 $g/m^2/24$ hrs, about 5000 $g/m^2/24$ hrs, about 5200 $g/m^2/24$ hrs, about 5400 $g/m^2/24$ hrs, about 5600 $g/m^2/24$ hrs, about 5800 $g/m^2/24$ hrs, about 6000 $g/m^2/24$ hrs, about 6200 $g/m^2/24$ hrs, about 6400 $g/m^2/24$ hrs, about 6600 $g/m^2/24$ hrs, about 6800 $g/m^2/24$ hrs, about 7000 $g/m^2/24$ hrs, about 7200 $g/m^2/24$ hrs, about 7400 $g/m^2/24$ hrs, about 7600 $g/m^2/24$ hrs, about 7800 $g/m^2/24$ hrs, about 8000 $g/m^2/24$ hrs, about 8200 $g/m^2/24$ hrs, about 8400 $g/m^2/24$ hrs, about 8600 $g/m^2/24$ hrs, about 8800 $g/m^2/24$ hrs, about 9000 $g/m^2/24$ hrs, about 9200 $g/m^2/24$ hrs, about 9400 $g/m^2/24$ hrs, about 9600 $g/m^2/24$ hrs, about 9800 $g/m^2/24$ hrs, about 10000 $g/m^2/24$ hrs, about 10500 $g/m^2/24$ hrs, about 11000 $g/m^2/24$ hrs, about 11500 $g/m^2/24$ hrs, about 12000 $g/m^2/24$ hrs, about 12500 $g/m^2/24$ hrs, about 13000 $g/m^2/24$ hrs, about 13500 $g/m^2/24$ hrs, about 14000 $g/m^2/24$ hrs, about 14500 $g/m^2/24$ hrs, about 15000 $g/m^2/24$ hrs, about 15500 $g/m^2/24$ hrs, about 16000 $g/m^2/24$ hrs, about 16500 $g/m^2/24$ hrs, about 17000 $g/m^2/24$ hrs, about 17500 $g/m^2/24$ hrs, about 18000 $g/m^2/24$ hrs, about 18500 $g/m^2/24$ hrs, about 19000 $g/m^2/24$ hrs, about 19500 $g/m^2/24$ hrs, about 20000 $g/m^2/24$ hrs, or any range including and/or in between any two of the preceding values. Such moisture vapor transmission rates allow the wound under the wound dressing to heal under moist conditions without causing the skin surrounding the wound to macerate.

Additionally or alternatively, in some embodiments, the third layer extends over each of the first layer, the second layer and optionally the fourth layer, such that a marginal region of width about 1 mm to about 50 mm, or about 5 mm to about 20 mm extends around wound dressing composition. In such cases, the wound-facing side of the extended region of the third layer is suitably coated with a pressure sensitive medical grade adhesive in at least its marginal region. Additionally or alternatively, the marginal region of the third layer comprise a width of about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 22 mm, about 24 mm, about 26 mm, about 28 mm, about 30 mm, about 32 mm, about 34 mm, about 36 mm, about 38 mm, about 40 mm, about 42 mm, about 44 mm, about 46 mm, about 48 mm, about 50 mm, or any range including and/or in between any two of the preceding values.

The Fourth Layer

The present disclosure provides a wound dressing composition optionally comprising a fourth layer wherein the fourth layer comprises a wicking layer.

In any embodiment disclosed herein, the fourth layer comprises a wound-facing side and an environmental-facing side.

In any embodiment disclosed herein, the wicking layer of the fourth layer is selected from the group consisting of a superabsorbent polymer, a non-woven carboxymethyl cellulose (CMC) pad, polyester, rayon, nylon, or any combination thereof. Additionally or alternatively, in some embodiments, the superabsorbent polymer of the material of the fourth layer is sodium polyacrylate. Additionally or alternatively, in some embodiments, the material of the fourth layer may comprise about 5 wt. % to about 100 wt. %. Additionally or alternatively, the material of the fourth layer may comprise about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, about 52 wt. %, about 54 wt. %, about 56 wt. %, about 58 wt. %, about 60 wt. %, about 62 wt. %, about 64 wt. %, about 66 wt. %, about 68 wt. %, about 70 wt. %, about 72 wt. %, about 74 wt. %, about 76 wt. %, about 78 wt. %, about 80 wt. %, about 82 wt. %, about 84 wt. %, about 86 wt. %, about 88 wt. %, about 90 wt. %, about 92 wt. %, about 94 wt. %, about 96 wt. %, about 98 wt. %, about 100 wt. %, or any range including and/or in between any two of the preceding values. Additionally or alternatively, in some embodiments, the thickness of the fourth layer may be in the range of about 15 μm to about 500 μm. Additionally or alternatively, in some embodiments, the thickness of the fourth layer may be in the range of about 15 μm, about 16 μm, about 17 μm, about 18 μm, about 19 μm, about 20 μm, about 22 μm, about 24 μm, about 26 μm, about 28 μm, about 30 μm, about 32 μm, about 34 μm, about 36 μm, about 38 μm, about 40 μm, about 42 μm, about 44 μm, about 46 μm, about 48 μm, about 50 μm, about 52 μm, about 54 μm, about 56 μm, about 58 μm, about 60 μm, about 62 μm, about 64 μm, about 66 μm, about 68 μm, about 70 μm, about 72 μm, about 74 μm, about 76 μm, about 78 μm, about 80 μm, about 82 μm, about 84 μm, about 86 μm, about 88 μm, about 90 μm, about 92 μm, about 94 μm, about 96 μm, about 98 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, or any range including and/or in between any two of the preceding values.

In any embodiment disclosed herein, the fourth layer may comprise a hydrophilic gradient to direct wound exudate and metabolites toward the second layer of the wound dressing composition, i.e. the reaction pad.

The Diagnostic Wound Dressing

The present disclosure provides a wound dressing composition comprising a first layer, a second layer, a third layer, and optionally a fourth layer, wherein each of the first layer, the second layer, the third layer and optionally the fourth layer comprise a wound-facing side and an environmental-facing side.

In some embodiments, the wound-facing side of the third layer is coupled with the environmental-facing side of the second layer, and wherein the wound-facing side of the second layer is coupled with the environmental-facing side of the first layer.

In some embodiments, the wound-facing side of the third layer is coupled with the environmental-facing side of the second layer, wherein the wound-facing side of the second layer is coupled with the environmental-facing side of the fourth layer, and wherein the wound-facing side of the fourth layer is coupled with the environmental-facing side of the first layer.

In any embodiment disclosed herein, the wound dressing composition comprises an indicator strip on the environmental facing side of the third layer to detect the presence of nitric oxide in the wound. Additionally or alternatively, the indicator strip may be composed of metal, paper, plastic, or any combination thereof. Additionally or alternatively, in some embodiments, the indicator strip may contain numerical values, evenly spaced hashes, or a color gradient where each color is correlated with a quantity of nitric oxide released. Additionally or alternatively, in some embodiments, the packaging may contain instructions to interpret the indicator strip.

In any embodiment disclosed herein, the wound dressing composition of the present disclosure is sterile and packaged in a microorganism-impermeable container. Additionally or alternatively, in some embodiments, the microorganism-impermeable container comprises an indicator strip to detect the presence of nitric oxide in the wound.

Detection and Treatment Methods of the Present Technology

In one aspect, the present disclosure provides a method of detecting levels of nitric oxide in wound in a subject in need thereof, wherein the method comprises administering to the wound a wound dressing composition of any embodiment described herein, and detecting a colorimetric change in the second layer, wherein the colorimetric change indicates the presence of nitric oxide in the wound. Additionally or alternatively, in some embodiments, the wound may be an acute wound or a chronic wound. Additionally or alternatively, in some embodiments, the wound is an acute wound selected from the group consisting of surgical wounds, trauma wounds, burns, graft sites, and donor sites. Additionally or alternatively, the wound is a chronic wound selected from the group consisting of infectious wounds, venous ulcers, arterial ulcers, ischemic ulcers, decubitis ulcers, and diabetic ulcers.

Any method known to those in the art for administering a wound dressing composition to an acute wound or a chronic wound disclosed herein may be employed. Suitable methods include in vitro or in vivo methods. In vivo methods typically include the administration of one or more wound dressing compositions to a subject in need thereof, suitably a human.

In any embodiment disclosed herein, the method of detecting nitric oxide in the wound further comprises determining the presence of nitric oxide in a wound by comparing colorimetric changes to the second layer of the wound dressing composition with an indicator strip on the environmental-facing side of the third layer. Additionally or alternatively, the method of detecting nitric oxide in the wound further comprises determining the presence of nitric oxide in a wound by comparing colorimetric changes to the second layer of the wound dressing composition with an indicator strip on the microorganism-impermeable container. In any embodiment disclosed herein, high levels of nitric oxide in the wound will point to a high colorimetric change in the reaction pad of the second layer. In any embodiment disclosed herein, low levels of nitric oxide in the wound will point to a low colorimetric change in the reaction pad of the second layer.

In any embodiment disclosed herein, the method of detecting nitric oxide in the wound further comprises determining the presence of nitric oxide in a wound by receiving an image of the colorimetric change of the second layer from an image capture device, comparing a value of at least one feature of the image to a threshold value, and providing an output responsive to comparing the value of the at least one feature to the threshold value, wherein the output is indicative of wound healing status.

In any embodiment disclosed herein, the method of detecting nitric oxide in the wound further comprises determining a first nitric oxide level upon administering the wound dressing composition to the wound, followed by determining a second nitric oxide level about 1 minute to about 24 hours after administering the wound dressing composition. Additionally or alternatively, wound healing status is determined when the second nitric oxide level is greater than the first nitric oxide level.

In another aspect, the present disclosure provides a method for monitoring the efficacy of a therapeutic intervention for a subject in need thereof, wherein the method comprises administering to the wound a wound dressing composition of any embodiment disclosed herein, detecting a colorimetric change in the second layer, wherein the colorimetric change indicates the presence of nitric oxide in the wound, determining a first nitric oxide level when the wound dressing composition is administered to the subject in need thereof, and determining a second nitric oxide level about 1 minute to about 24 hours after the wound dressing composition is administered to the subject in need thereof, wherein the therapeutic intervention is effective when the second nitric oxide level is greater compared to the first nitric oxide level.

In another aspect, the present disclosure provides a method for monitoring the efficacy of a therapeutic intervention for a subject in need thereof, wherein the method comprises administering to the wound a wound dressing composition of any embodiment disclosed herein, determining a nitric oxide level when the wound dressing composition is administered to the subject in need thereof, wherein the therapeutic intervention is effective when the nitric oxide level is increased relative to a pre-determined reference level. Additionally or alternatively, in some embodiments, a pre-determined reference level can be set by a person of ordinary skill in the art at 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 22 minutes, 24 minutes, 26 minutes, 28 minutes, 30 minutes, 32 minutes, 34 minutes, 36 minutes, 38 minutes, 40 minutes, 42 minutes, 44 minutes, 46 minutes, 48 minutes, 50 minutes, 52 minutes, 54 minutes, 56 minutes, 58 minutes, 60 minutes, or any range including and/or in between any two of the preceding values.

In any embodiment of the methods of the present technology, a composition comprising a wound dressing composition disclosed herein, is administered to the subject. Without wishing to be bound by theory, it is believed that, the wound exudate of the subject may vary in viscosity and quantity, thus affecting the appropriate temporal window for administering the wound dressing compositions disclosed herein. Additionally or alternatively, in some embodiments, the diffusion rate of the wound exudate may vary depending on the structure of the wound dressing composition disclosed herein. Additionally or alternatively, in some embodiments, the wound dressing compositions are administered for about 1 minute or more. Additionally or alternatively, in some embodiments, the wound dressing compositions are administered for about 1 minute, about 2 minutes, about 3 minutes, about 4 minutes, about 5 minutes, about 6 minutes, about 7 minutes, about 8 minutes, about 9 minutes, about 10 minutes, or more. Additionally or alternatively, in some embodiments, the wound dressing compositions are administered for about 10 minutes, about 11 minutes, about 12 minutes, about 13 minutes, about 14 minutes, about 15 minutes, about 16 minutes, about 17 minutes, about 18 minutes, about 19 minutes, about 20 minutes, or more. Additionally or alternatively, in some embodiments, the wound dressing compositions are administered for about 20 minutes, about 22 minutes, about 24 minutes, about 26 minutes, about 28 minutes, about 30 minutes, about 32 minutes, about 34 minutes, about 36 minutes, about 38 minutes, about 40 minutes, about 42 minutes, about 44 minutes, about 46 minutes, about 48 minutes, about 50 minutes, about 52 minutes, about 54 minutes, about 56 minutes, about 58 minutes, about 1 hour, or more. Additionally or alternatively, in some embodiments, the wound dressing compositions are administered for about 1 hour, about 2 hour, about 3 hour, about 4 hour, about 5 hour, about 6 hour, about 7 hour, about 8 hour, about 9 hour, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or more.

Methods of Making the Wound Dressing of the Present Technology

Also disclosed herein are methods for making the wound dressing compositions of the present technology. In one aspect, the present disclosure provides a method for making a wound dressing composition comprising, providing a first layer comprising an absorbent pad, providing a second layer comprising a reaction pad, providing a third layer comprising a transparent backing film, and combining the first layer, the second layer, and the third layer to form the wound dressing composition, wherein each of the first layer, the second layer, and the third layer comprises a wound-facing side and an environmental-facing side. In another aspect, the present disclosure provides a method for making a wound dressing composition comprising, providing a first layer comprising an absorbent pad, providing a second layer comprising a reaction pad, providing a third layer comprising a transparent backing film, providing a fourth layer comprising a wicking layer, and combining the first layer, the second layer, the third layer, and the fourth layer to make the wound dressing composition, wherein each of the first layer, the second layer, the third layer, and the fourth layer comprises a wound-facing side and an environmental-facing side. In one example, a first layer comprising a hydrophilic foam pad (e.g., polyurethane foam) is configured to interface with a wound surface. The foam layer may be backed with a superabsorbent or a wicking layer material of equal size or smaller size compared to the foam component. When the size of the superabsorbent or wicking layer material are equal to that of the foam component, the superabsorbent or wicking layer material may be adjoined via a process such as lamination, or by utilizing an adhesive. Alternatively, where the size of the superabsorbent or wicking layer is smaller than the foam layer, no adhesion between the two adjoining layers is required. The second layer comprising a reaction pad will generally be smaller in size. The reaction pad may be composed of a range of carrier materials including, but not limited to a gauze or filter paper. The reaction components are coated/incorporated into the reaction pad. Coating/incorporation may be conducted using a range of methods such as dehydration of a solution comprising the reaction components on to the carrier material. Alternatively, the deposited reaction components may be kept separate on the reaction pad using pattern coating (e.g., alternate stripes or dots). The exterior third layer comprises a breathable protective backing film that permits evaporation to occur, whilst preventing contamination of the wound. An adhesive coating may be present on the wound facing side of the third layer, which acts to secure the entire wound dressing to the wound and also adheres to the environmental-facing side of the fourth layer (comprising the absorbent or wicking layer component) and/or the second layer (comprising the reaction pad) thus holding the dressing together. In a further embodiment, a colorimetric indicator strip may be included for ease of assessment. In terms of dressing construction, the colorimetric indicator strip may be printed directly onto the third layer (comprising the backing film component) or placed onto the third layer as a separate component that is held in place with an adhesive.

Kits Comprising the Diagnostic Wound Dressing of the Present Technology

In a further related aspect, the present disclosure provides kits that include a wound dressing composition of any embodiment described herein and instructions for use. The kits of the present technology may also include methods for treating a wound in a subject in need thereof. The kits of the present technology may also include an indicator strip to detect the presence of nitric oxide in a wound. The kit may optionally comprise components such as antiseptic wipes, ointment, adhesive tape, tweezers, or scissors.

EXPERIMENTAL EXAMPLES

The present technology is further illustrated by the following examples, which should not be construed as limiting in any way.

Example 1: Detecting Nitric Oxide Levels in a Wound

A wound dressing composition comprising a first layer, a second layer, a third layer, and optionally a fourth layer as described in any embodiment herein (FIG. 1) will be assembled as disclosed herein. The wound dressing composition will be administered directly to a chronic wound, with the wound-facing side of the first layer contacting the wound. A first nitric oxide level will be determined by comparing the colorimetric change of the reaction pad to the indicator strip on the environmental-facing side of the third layer after administering the wound dressing composition to the wound. A second nitric oxide level will be determined by comparing the colorimetric change of the reaction pad to the indicator strip on the environmental-facing side of the third layer about 1 minute to about 24 hours after administering the wound dressing composition to the wound. The time of administration of the wound dressing composition will be determined by the amount of exudate in the wound. It is anticipated that administration of the wound dressing composition to a chronic wound will result in the detection of nitric oxide levels in the wound, an indication of wound healing status.

These results will demonstrate that the wound dressing compositions of the present technology are useful for detecting nitric oxide levels in a wound in a subject in need thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all FIGURES and tables, to the extent they are not inconsistent with the explicit teachings of this specification.

The invention claimed is:

1. A wound dressing composition comprising a first layer, a second layer, and a third layer:

wherein each of the first layer, the second layer, and the third layer comprises a wound-facing side and an environmental-facing side;

wherein the first layer comprises an absorbent layer;

wherein the second layer comprises a reaction pad including a first reagent configured to react with a second reagent to provide a first color intensity change indicating the presence of nitric oxide, wherein the first reagent is further configured to react with the second reagent to provide a second color intensity change, with continued exposure to wound fluid in the wound dressing, after the first color intensity change, and wherein a ratio of the first reagent to the second reagent is about 10:1; and wherein the third layer comprises a transparent backing film, and wherein the second layer is positioned between the first layer and the third layer, the third layer further comprising a colorimetric indicator strip including a plurality of colors correlated to a quantity of nitric oxide indicated by the first color intensity change and the second color intensity change of the second layer, wherein the plurality of colors include at least a first color intensity correlating to a first nitric oxide quantity, a second color intensity correlating to a second nitric oxide quantity that is greater than the first nitric oxide quantity, and a third color intensity correlating to a third nitric oxide quantity that is greater than the first nitric oxide quantity and the second nitric oxide quantity.

2. The wound dressing composition of claim 1, further comprising a fourth layer:

wherein the fourth layer comprises a wound-facing side and an environmental-facing side; and wherein the fourth layer comprises a wicking layer, wherein the wound-facing side of the third layer is coupled with the environmental-facing side of the second layer, wherein the wound-facing side of the second layer is coupled with the environmental-facing side of the fourth layer, and wherein the wound-facing side of the fourth layer is coupled with the environmental-facing side of the first layer.

3. The wound dressing composition of claim 2, wherein the fourth layer is selected from the group consisting of a superabsorbent polymer, a non-woven carboxymethyl cellulose (CMC) pad, polyester, rayon, nylon, or any combination thereof.

4. The wound dressing composition of claim 1, wherein the first layer is selected from the group consisting of a foam pad, a gauze, a nonwoven fabric, a superabsorbent, a hydrogel, and any combination thereof, optionally wherein the foam pad is a polyurethane foam pad.

5. The wound dressing composition of claim 1, wherein the third layer is selected from the group consisting of polyurethane, polyalkoxy alkyl acrylate, polyalkoxy alkyl methacrylate, and any combination thereof, optionally wherein the colorimetric indicator strip is included on the environmental-facing side of the third layer.

6. The wound dressing composition of claim 1, wherein the second layer is selected from the group consisting of a gauze, a nonwoven fabric, a filter paper, and any combination thereof.

7. The wound dressing composition of claim 1, wherein the second layer comprises a dried reaction mixture of the first reagent and the second reagent, wherein the first reagent has the formula:

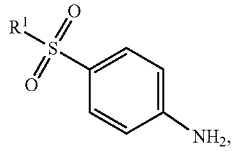

wherein $R^1$ is $NH_2$ or OH, and wherein the second reagent has the formula:

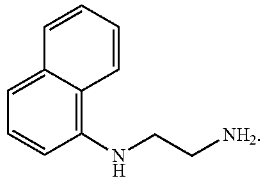 [SMILES: NCCNc1cccc2ccccc12]

8. The wound dressing composition of claim 1, wherein the thickness of each the first layer and the second layer is independently about 15 μm to about 500 μm, and/or wherein the thickness of the third layer is about 10 μm to about 1000 μm, about 15 μm to about 500 μm, or about 100 μm to about 500 μm.

9. The wound dressing composition of claim 1, wherein the colorimetric indicator strip is coupled to the environmental-facing side of the third layer, wherein the third layer extends beyond each of the first layer and the second layer such that a marginal region of width extends around the wound dressing composition from about 1 mm to about 50 mm, or about 5 mm to about 20 mm, optionally wherein the wound-facing side of the extended region of the third layer is coated with a pressure sensitive medical grade adhesive.

10. The wound dressing composition of claim 1, wherein the wound dressing composition is sterile and packaged in a microorganism-impermeable container.

11. A method for detecting nitric oxide levels in a wound in a subject in need thereof, comprising:

administering to the wound a wound dressing composition of claim 1; and detecting a colorimetric change in the second layer, wherein the colorimetric change indicates the presence of nitric oxide in the wound.

12. The method of claim 11, further comprising determining nitric oxide levels by comparing the color of the second layer to the indicator strip located on the third layer.

13. The method of claim 11, further comprising determining nitric oxide levels by comparing the color of the second layer to an indicator strip present on a microorganism-impermeable container for the wound dressing composition.

14. The method of claim 11, further comprising determining nitric oxide levels by:

receiving an image from an image capture device;

comparing a value of at least one feature of the image to a threshold value; and providing an output responsive to comparing the value of the at least one feature to the threshold value; and wherein the output is indicative of wound healing status.

15. The method of claim 11, further comprising:

determining a first nitric oxide level when the wound dressing composition is administered to the subject in need thereof; and determining a second nitric oxide level about 1 minute to about 24 hours after the wound dressing composition is administered to the subject in need thereof.

16. A method for monitoring the efficacy of a therapeutic intervention for a subject in need thereof, comprising:

administering to the wound a wound dressing composition of claim 1;

detecting a colorimetric change in the second layer, wherein the colorimetric change indicates the presence of nitric oxide in the wound;

determining a first nitric oxide level when the wound dressing composition is administered to the subject in need thereof; and determining a second nitric oxide level about 1 minute to about 24 hours after the wound dressing composition is administered to the subject in need thereof, wherein the therapeutic intervention is effective when the second nitric oxide level is greater compared to the first nitric oxide level.

17. A method for monitoring the efficacy of a therapeutic intervention for a subject in need thereof, comprising:

administering to the wound a wound dressing composition of claim 1;

detecting a colorimetric change in the second layer, wherein the colorimetric change indicates the presence of nitric oxide in the wound; and determining a nitric oxide level when the wound dressing composition is administered to the subject in need thereof;

wherein the therapeutic intervention is effective when the nitric oxide level is increased compared to a pre-determined reference level.

18. A method for making a wound dressing composition comprising:

providing a first layer, a second layer, and a third layer; and combining the first layer, the second layer, and the third layer to make the wound dressing composition, wherein each of the first layer, the second layer, and the third layer comprises a wound-facing side and an environmental-facing side;

wherein the first layer comprises an absorbent pad;

wherein the second layer comprises a reaction pad; and wherein the third layer comprises a transparent backing film.

19. A method for making a wound dressing composition comprising:

providing a first layer, a second layer, a third layer, and a fourth layer; and combining the first layer, the second layer, the third layer, and the fourth layer to make the wound dressing composition, wherein each of the first layer, the second layer, the third layer, and the fourth layer comprises a wound-facing side and an environmental-facing side;

wherein the first layer comprises an absorbent pad;

wherein the second layer comprises a reaction pad;

wherein the third layer comprises a transparent backing film; and wherein the fourth layer comprises a wicking layer.

20. A kit comprising the wound dressing composition of claim 1, an indicator strip for determining nitric oxide levels in a wound, and instructions for use.

* * * * *